(12) United States Patent
Beasley, Jr.

(10) Patent No.: US 6,274,636 B1
(45) Date of Patent: Aug. 14, 2001

(54) METHOD FOR TREATING A TIC DISORDER

(75) Inventor: Charles M. Beasley, Jr., Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/242,418
(22) PCT Filed: Aug. 27, 1996
(86) PCT No.: PCT/US96/14090
  § 371 Date: Feb. 16, 1999
  § 102(e) Date: Feb. 16, 1999
(87) PCT Pub. No.: WO97/11700
  PCT Pub. Date: Apr. 3, 1997

Related U.S. Application Data
(60) Provisional application No. 60/005,176, filed on Sep. 29, 1995.

(51) Int. Cl.[7] .................................................. A61K 31/55
(52) U.S. Cl. .......................................... 518/220; 514/974
(58) Field of Search ...................................... 514/220, 978

(56) References Cited

U.S. PATENT DOCUMENTS 5,776,928 * 7/1998 Beasely, Jr. ........................... 514/220
5,817,656 * 10/1998 Beasely, Jr. et al. ................. 514/220

* cited by examiner

Primary Examiner—Frederick Krass
(74) Attorney, Agent, or Firm—Arleen Palmberg; MaCharri Vorndran-Jones

(57) ABSTRACT

The invention provides a method for treating a tic disorder comprising administering an effective amount of 2-methyl-4-(4-methyl-1-piperazinyl)-10H-thieno[2,3-b][1,5]benzodiazepine.

9 Claims, No Drawings

METHOD FOR TREATING A TIC DISORDER

This application is a 371 of PCT/US96/14090, filed Aug. 27, 1996, and claims the benefit of U.S. Provisional Application No. 60/005,176, filed Sep. 29, 1995.

This invention provides a method for using 2-methyl-4-(4-methyl-1-piperazinyl)-10H-thieno[2,3-b][1,5]benzodiazepine, for the treatment of a tic disorder featuring one or more vocal tics.

A tic is a sudden, rapid, recurrent, nonrhythmic, stereotyped motor movement or vocalization. A tic is experienced as irresistible but can be suppressed for varying lengths of time. Common simple motor tics include eye blinking, neck jerking, shoulder shrugging, facial grimacing, and coughing. Common simple vocal tics include throat clearing, grunting, sniffing, snorting, and barking. Common complex motor tics include facial gestures, grooming behaviors, jumping, touching, stamping, and smelling an object. Common complex vocal tics include repeating words or phrases out of context, coprolalia (use of socially unacceptable words, frequently obscene), palilalia (repeating one's own sounds or words), and echolalia (repeating the last heard sound, word, or phrase).

Tic disorders are distinguished from compulsions because compulsions are complex and performed in response to an obsession or according to rules that must be applied rigidly. In contrast to a compulsion, tics are typically less complex and are not aimed at neutralizing the anxiety resulting from an obsession.

Often tic disorders can be caused or exacerbated by the use of certain medications which may include antipsychotic agents. Diagnostic and Statistical Manual of Mental Disorders, Fourth Edition, (American Psychiatric Association, 1994) p 101. (Hereinafter, DSM-IV) Surprisingly, Applicant has discovered that 2-methyl-4-(4-methyl-1-piperazinyl)-10H-thieno[2,3-b][1,5] benzodiazepine can be useful for treating tic disorders featuring multiple motor tics and one or more vocal tics; one motor tic and one vocal tic; one motor tic and multiple vocal tics; and for vocal tics. Applicant unexpectedly discovered that 2-methyl-4-(4-methyl-1-piperazinyl)-10H-thieno[2,3-b)][1,5]benzodiazepine can be useful for treating not only movement tics but vocal tics as well.

It is known that the compound 2-methyl-4-(4-methyl-1-piperazinyl)-10H-thieno[2,3-b][1,5]benzodiazepine can provide antipsychotic activity and is less likely to induce extrapyramidal symptoms. However, Applicant has discovered that 2-methyl-4-(4-methyl-1-piperazinyl)-10H-thieno[2,3-b][1,5]benzodiazepine can be useful for treating a vocal tic disorder which may feature one or more motor tics as well. The method of use claimed herein may provide the longed for new treatment option for a tic disorder, wherein, 2-methyl-4-(4-methyl-1-piperazinyl)-10H-thieno[2,3-b][1,5]benzodiazepine has demonstrated a favorable safety profile in human clinical trials. The compound 2-methyl-4-(4-methyl-1-piperazinyl)-10H-thieno[2,3-b][1,5]benzodiazepine is known and described in U.S. Pat. No. 5,229,382, herein incorporated by reference in its entirety.

The presently claimed invention provides a method for treating a tic disorder comprising administering an effective amount of 2-methyl-4-(4-methyl-1-piperazinyl)-10H-thieno[2,3-b][1,5]benzodiazepine or a pharmaceutically acceptable salt thereof to a patient in need of such treatment.

The present invention further provides the use of 2-methyl-4-(4-methyl-1-piperazinyl)-10H-thieno[2,3-b][1,5]benzodiazepine for the manufacture of a medicament for the treatment of a tic disorder.

Additionally, the invention provides a formulation adapted for the treatment of a tic disorder containing 2-methyl-4-(4-methyl-1-piperazinyl)-10H-thieno[2,3-b][1,5]benzodiazepine.

It is preferred that 2-methyl-4-(4-methyl-1-piperazinyl)-10H-thieno[2,3-b][1,5]benzodiazepine is anhydrous Form II.

The 2-methyl-4-(4-methyl-1-piperazinyl)-10H-thieno[2,3-b][1,5]benzodiazepine compound is of the formula

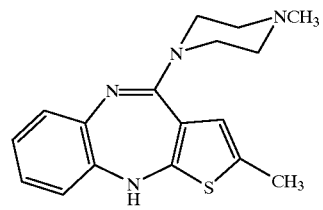

or an acid addition salt thereof. The free base of the above compound is 2-methyl-4-(4-methyl-1—piperazinyl)-10H-thieno[2,3-b][1,5]benzodiazepine.

The substantially pure crystalline anhydrous Form II 2-methyl-4-(4-methyl-1-piperazinyl)-10H-thieno[2,3-b][1,5]benzodiazepine (Form II) has a typical X-ray powder diffraction pattern substantially as follows, using a Sieman's D5000 diffractometer equipped with a copper radiation source, wherein d represents the interplaner spacing:

| d | I/I$_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

Form I 2-methyl-4-(4-methyl-1-piperazinyl)-10H-thieno[2,3-b][1,5]benzodiazepine (Form I) has a typical x-ray powder diffraction pattern substantially as follows, using a Sieman's D5000 diffractometer equipped with a copper radiation source, wherein d represents the interplaner spacing:

| d | I/I$_1$ |
|---|---|
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |
| 5.5895 | 1.10 |
| 5.3055 | 0.95 |
| 4.9815 | 6.14 |
| 4.8333 | 68.37 |
| 4.7255 | 21.88 |
| 4.6286 | 3.82 |
| 4.533 | 17.83 |
| 4.4624 | 5.02 |
| 4.2915 | 9.19 |
| 4.2346 | 18.88 |
| 4.0855 | 17.29 |
| 3.8254 | 6.49 |
| 3.7489 | 10.64 |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

The x-ray powder diffraction patterns set forth herein were obtained with a copper K of wavelength=1.541A. The interplaner spacings in the column marked "d" are in Angstroms. The typical relative intensities are in the column marked "I/I$_1$". The detector was a Kevex silicon lithium solid state detector.

As used herein "substantially pure" shall refer to anhydrous Form II associated with <5% Form I; and most preferably it shall refer to <2% Form I. It is further preferred that "substantially pure" shall refer to <0.5% non-Form II polymorph.

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

As used herein, the term "tic disorder" or "tic disorders" shall include tic disorders featuring multiple motor tics and one or more vocal tics; one motor tic and one vocal tic; one motor tic and multiple vocal tics; and for vocal tic(s). Examples include, but are not limited to, Transient Tic Disorder, Tourette's Disorder, Chronic Vocal Tic Disorder, and Tic Disorder not otherwise specified as described by DSM-IV, page 101. It is particularly preferred that the term refers to Tourette's Disorder.

The results of pharmacological studies show that 2-methyl-4-(4-methyl-1-piperazinyl)-10H-thieno[2,3-b][1,5]benzodiazepine has muscarinic cholinergic receptor activity. The compound is active at the dopamine D-1 and D-2 receptors as indicated by an IC50 of less than 1 uM in the 3H-SCH233390 (Billard, et al. Life Sciences 35:1885 (1984)) and the 3H spiperone (Seeman, et al. Nature 216:717 (1976)) binding assays respectively. Further, the anhydrous Form II compound is active at the 5-HT-2 receptor and 5-HT1C receptor. The complex pharmacological profile of the compound provides a medicament which can be useful for the treatment of a tic disorder.

In vivo animal and clinical observations support that 2-methyl-4-(4-methyl-1-piperazinyl)-10H-thieno[2,3-b][1,5]benzodiazepine has a complex muscarinic receptor subtype profile. For example, rats exposed to an overdose of the compound surprisingly exhibited significant salivation. Further, clinical subjects experienced pupilary constriction rather than the expected pupilary dilation.

The usefulness of the compound for treating various tic disorders can be supported by the following studies as described.

I. Inhibition of Thalamonal-Induced Rigor in Rats.

Rigor is induced in male and female rats (Sprague Dawley strain) by the administration of 7.5 mg/kg of Thalainonal (2.5 mg/ml droperidol and 0.5 mg/ml fentanyl). After 15 minutes each test animal is immobilized in a hammock and bipolar electrode inserted into the calf muscle of one limb. The electromyogram is recorded. Thirty minutes after administration of the Thalamonal, the 2-methyl-4-(4-methyl-1-piperazinyl)-10H-thieno[2,3-b][1,5]benzodiazepine compound is administered by i.v. injection into the tail vein in increasing doses at 10 intervals. Six rats are used per compound and the dose necessary to reduce the intensity of the rigor by 10% and the dose required to completely abolish the rigor are determined by comparison of the integrated electromyograms obtained before and after the administration of the 2-methyl-4-(4-methyl-1-piperazinyl)-10-thieno[2,3-b][1,5]benzodiazepine. A placebo control group, wherein the rats are injected with vehicle at 10 minute intervals, is included in the study.

II. Clinical Observations.

A double-blind multicenter clinical trial was designed to assess the safety and efficacy of 2-methyl-4-(4-methyl-1-piperazinyl)-10H-thieno[2,3-b][1,5]benzodiazepine in patients wherein one observation of the study was the effect of 2-methyl-4-(4-methyl-1-piperazinyl)-10H-thieno[2,3-b][1,5]benzodiazepine on patients with and without tic disorders at study entry. Patients were randomized to 2-methyl-4-(4-methyl-1-piperazinyl)-10H-thieno[2,3-b][1,5]benzodiazepine or placebo. The results of the study suggest that 2-methyl-4-(4-methyl-1-piperazinyl)-10H-thieno[2,3-b][1,5]benzodiazepine can be useful for the treatment of tic disorders.

The compound of 2-methyl-4-(4-methyl-1-piperazinyl)-10H-thieno[2,3-b][1,5]benzodiazepine can be prepared using the methods taught by U.S. Pat. No. 5,229,382.

The compound has an IC of less than 1 mM in the 3H-QNB binding assay described by Yamamura, HI and Snyder, SH in Proc. Nat. Acad. Sci. USA 71 1725 (1974) indicating that it has muscarinic-cholinergic activity.

The 2-methyl-4-(4-methyl-1-piperazinyl)-10H-thieno-[2,3-b][1,5]benzodiazepine compound is effective over a wide dosage range, the actual dose administered being dependent on the condition being treated. For example, in the treatment of adult humans, dosages of from about 0.25 to 50 mg, preferably from 1 to 30 mg, and most preferably 1 to 20 mg per day may be used. A once a day dosage is normally sufficient, although divided doses may be administered. For treatment of a tic disorder, a dose range of fro 1 to 30 mg, preferably 1 to 20 mg per day is suitable. Radiolabelled 2-methyl-4-(4-methyl-1-piperazinyl)-10H-thieno-[2,3-b][1,5]benzodiazepine, can be detected in the saliva and thus the compound can potentially be monitored in patients to assess compliance.

A preferred formulation of the invention is a solid oral formulation comprising from about 1 to about 20 mg or 1 to 10 mg of active anhydrous Form II 2-methyl-4-(4-methyl-1-piperazinyl)-10H-thieno[2,3-b][1,5]benzodiazepine as an effective amount of the active ingredient.

Most preferably, the solid oral formulation is contained in packaging materials which protect the formulation from moisture and light. For example, suitable packaging materials include amber colored high density polyethylene bottles, amber colored glass bottles, and other containers made of a material which inhibits the passage of light. Most preferably, the packaging will include a desiccant pack. The container may be sealed with an aluminum foil blister to provide the desired protection and maintain product stability.

The 2-methyl-4-(4-methyl-1-piperazinyl)-10H-thieno[2,3-b][1,5]benzodiazepine compound will normally be administered orally or by injection and, for this purpose, it is usually employed in the form of a pharmaceutical composition.

Accordingly, pharmaceutical compositions comprising 2-methyl-4-(4-methyl-1-piperazinyl)-10H-thieno[2,3-b][1,5]benzodiazepine, as active ingredient associated with a pharmaceutically acceptable carrier may be prepared. In making the compositions of the invention conventional techniques for the preparation of pharmaceutical compositions may be used. For example, the active ingredient will usually be mixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. the active ingredient can be adsorbed on a granular solid container for example in a sachet. Some examples of suitable carriers are lactose, dextrose, sucrose, sorbitol, mannitol, starches, gum acaia, calcium phosphate, alginates, tragacanth, gelatin, syrup, methyl cellulose, methyl- and propyl-hydroxy-benzoate, talc, magnesium stearate or mineral oil. The compositions of the invention may, if desired, be formulated so as to provide quick, sustained or delayed release of the active ingredient after administration to the patient. For example, one such preferred quick release formulation is described in U.S. Pat. Nos. 5,079,018, 5,039,540, 4,305,502, 4,758,598, and 4,371,516, hereby incorporated by reference. Such formulation most preferably comprises 2-methyl-4-(4-methyl-1-piperazinyl)-10H-thieno[2,3-b][1,5]benzodiazepine, water, hydrolyzed gelatin, and mannitol.

Depending on the method of administration, the compositions for the treatment of central nervous system conditions may be formulated as tablets, capsules, injection solutions for parenteral use, gel or suspension for transdermal delivery, suspensions or elixirs for oral use or suppositories. Preferably the compositions are formulated in a unit dosage form, each dosage containing from 0.25 to 100 mg, more usually 1 to 30 mg, of the active ingredient. When a sustained release formulation is desired, the unit dosage form may contain from 0.25 to 200 mg of the active ingredient. A preferred formulation of the invention is a capsule or tablet comprising 0.25 to 75 mg or 1 to 30 mg of active ingredient together with a pharmaceutically acceptable carrier therefor. A further preferred formulation is an injection which in unit dosage form comprises 0.25 to 30 mg or 1 to 30 mg of active ingredient together with a pharmaceutically acceptable diluent therefor. Another preferred formulation is 2-methyl-4-(4-methyl-1-piperazinyl)-10H-thieno[2,3-b][1,5]benzodiazepine in a transdermal formulation.

The materials for the present invention can be purchased or prepared by a variety of procedures well known to those of ordinary skill in the art. The 2-methyl-4-(4-methyl-1-piperazinyl)-10H-thieno[2,3-b][1,5]benzodiazepine compound can be prepared as described in Chakrabarti in U.S. Pat. No. 5,229,382 ('382), herein incorporated by reference in its entirety.

Compound characterization methods include, for example, x-ray powder pattern analysis, thermogravimetric analysis (TGA), differential scanning calorimetery (DSC), titrametric analysis for water, and $H^1$-NMR analysis for solvent content.

The following examples are provided for purposes of illustration and are not to be construed as limiting the scope of the claimed invention.

Preparation 1a

Technical Grade 2-methyl-4-(4-methyl-1-piperazinyl)-10H-thieno[2,3-b][1,5] benzodiazepine

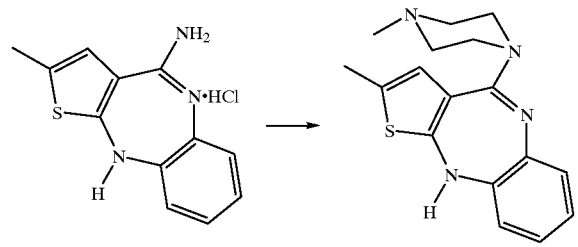

In a suitable three neck flask the following was added:

ylsulfoxide (analytical): 6 volumes

Intennediate 1: 75 g

N-Methlylpiperazine (reagent): 6 equivalents

Intermediate 1 can be prepared using methods known to the skilled artisan. For example, the preparation of the Intermediate 1 is taught in the '382 patent. A sub-surface nitrogen sparge line was added to remove the ammonia formed during the reaction. The reaction was heated to 120° C. and maintained throughout the duration of the reaction. The reactions were followed by HPLC until ≦5% of the intermediate 1 was left unreacted. After the reaction was complete, the mixture was allowed to cool slowly to 20° C. (about. 2 hours) Each reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical 2-methyl-4-(4-methyl-1-piperazinyl)-10H-thieno[2,3-b][1,5] benzodiazepine.

Yield: 76.7%; Potency: 98.1%

Preparation 1b

Form II

A 270 g sample of technical grade 2-methyl-4-(4-methyl-1-piperazinyl)-10H-thieno[2,3-b][1,5] benzodiazepine was suspended in ethyl acetate (2.7 L). The mixture was heated to about 76° C. and maintained at about 76° C. for about 30 minutes. The mixture was allowed to cool to about 25° C. The resulting product was isolated using vacuum filtration. The product was identified as Form II 2-methyl-4-(4-methyl-1-piperazinyl)-10H-thieno[2,3-b][1,5] benzodiazepine using x-ray powder analysis.

Yield: 197 g.

EXAMPLE 1

A portion of the hydroxypropyl cellulose was dissolved in purified water to form a solution for granulation. The remaining hydroxypropyl cellulose (total of 4.0% w/w final tablet weight), which was an extra fine grade, was combined with the 2-methyl-4-(4-methyl-1-piperazinyl)-10H-thieno[2,3-b][1,5]benzodiazepine (1.18% w/w), lactose (79.32% w/w) and a portion of the crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer.

The running powders consisting of microcrystalline cellulose (granular) (10% w/w), magnesium stearate (0.5% w/w), and the remainder of the crospovidone were added to the sized granulator. The mixture was blended and compressed with the appropriate tooling on tablet compression equipment.

Subcoating:

Hydroxypropyl methylcellulose (10% w/w) was mixed with purified water to form a solution. Core tablets were divided into approximately equal sections and spray coated with the hydroxypropyl methylcellulose solution. The operation was performed in a perforated coating pan.

Coating of Core Tablets:

Color Mixture White (hydroxypropyl methylcellulose, polyethylene glycol, polysorbate 80, and titanium dioxide) was mixed with purified water to form the coating suspension. Subcoated tablets were divided into approximately equal sections and spray coated with the coating suspension described above. The operation was performed in a perforated coating pan.

The coated tablets were lightly dusted with carnauba wax and imprinted with appropriate identification.

EXAMPLE 2

The process substantially as described above in Example 1 was repeated using the following ingredients to provide pharmaceutically elegant tablet formulations containing 1, 2.5, 5, 7.5, and 10 mg 2-methyl-4-(4-methyl-1-piperazinyl)-10H-thieno[2,3-b][1,5]benzodiazepine, respectively, per tablet:

1 mg 2-methyl-4-(4-methyl-1-piperazinyl)-10H-thieno[2,3-b][1,5benzodiazepine per tablets:

| Names of Ingredients | Quantity (mg/tablet) |
|---|---|
| Active Ingredient | |
| 2-methyl-4-(4-methyl-1-piperazinyl)-10H-thieno[2,3-b] [1,5] benzodiazepine | 1.0 |
| Other Ingredients | |
| Lactose | 67.43 |
| Hydroxypropyl Cellulose | 3.40 |
| Crospovidone | 4.25 |
| Microcrystalline Cellulose | 8.50 |
| Magnesium Stearate | 0.42 |
| Subcoatiug Hydroxypropyl Methylcellulose Coating | 1.70 |
| Color Mixture White Coating | 3.47 |
| Polishing Carnauba Wax | trace |
| Imprinting Edible Blue Ink | trace |

2-methyl-4-(4-methyl-1-piperazinyl)-10H-thieno[2,3-b][1,5]benzodiazepine 2.5 mg tablets:

| Names of Ingredients | Quantity (mg/tablet) |
|---|---|
| Active Ingredient | |
| 2-methyl-4-(4-methyl-1-piperazinyl)-10H-thieno[2,3-b] [1,5] benzodiazepine | 2.5 |
| Other Ingredients | |
| Lactose | 102.15 |
| Hydroxypropyl Cellulose | 5.20 |
| Crospovidone | 6.50 |
| Microcrystalline Cellulose | 13.00 |
| Magnesium Stearate | 0.65 |
| Subcoating Hydroxypropyl Methylcellulose | 2.60 |
| Coating Color Mixture White | 5.30 |
| Polishing Carnauba Wax | trace |
| Imprinting Edible Blue Ink | trace |

2-methyl-4-(4-methyl-1-piperazinyl)-10H-thieno[2,3-b][1,5]benzodiazepine 5.0 mg tablets:

| Names of Ingredients | Quantity (mg/tablet) |
|---|---|
| Active Ingredient | |
| 2-methyl-4-(4-methyl-1-piperazinyl)-10H-thieno[2,3-b] [1,5] benzodiazepine | 5.0 |
| Other Ingredients | |
| Lactose | 156.00 |
| Hydroxypropyl Cellulose | 8.00 |
| Crospovidone | 10.00 |
| Microcrystalline Cellulose | 20.00 |
| Magnesium Stearate | 1.00 |
| Subcoating | 4.00 |
| Hydroxypropyl Methylcellulose Coating | 8.16 |
| Color Mixture White Polishing Carnauba Wax | trace |
| Imprinting Edible Blue Ink | trace |

2-methyl-4-(4-methyl-1-piperazinyl)-10H-thieno[2,3-b][1,5]benzodiazepine 7.5 mg tablets:

| Names of Ingredients | Quantity (mg/tablet) |
|---|---|
| Active Ingredient | |
| 2-methyl-4-(4-methyl-1-piperazinyl)-10H-thieno[2,3-b][1,5]benzodiazepine | 7.50 |
| Other Ingredients | |
| Lactose | 234.00 |
| Hydroxypropyl Cellulose | 12.00 |
| Crospovidone | 15.00 |
| Microcrystalline Cellulose | 30.00 |
| Magnesium Stearate | 1.50 |
| Subcoating Hydroxypropyl Methylcellulose | 6.00 |
| Coating | 12.24 |
| Color Mixture White Polishing Carnauba Wax | trace |
| Imprinting Edible Blue Ink | trace |

2-methyl-4-(4-methyl-1-piperazinyl)-10H-thieno[2,3-b][1,5]benzodiazepine 10.0 mg tablets:

| Names of Ingredients | Quantity (mg/tablet) |
|---|---|
| Active Ingredient | |
| 2-methyl-4-(4-methyl-1-piperazinyl)-10H-thieno[2,3-b][1,5]benzodiazepine | 10.0 |
| Other Ingredients | |
| Lactose | 312.00 |
| Hydroxypropyl Cellulose | 16.00 |
| Crospovidone | 20.00 |
| Microcrystalline Cellulose | 40.00 |
| Magnesium Stearate | 2.00 |
| Subcoating Hydroxypropyl Methylcellulose | 8.00 |
| Coating | 16.32 |
| Color Mixture White Polishing Carnauba Wax | trace |
| Imprinting Edible Blue Ink | trace |

EXAMPLE 4

Pulvule Formulation

A pulvule formulation is prepared by blending the active with silicone starch, and filling it into hard gelatin capsules.

| | Per 300 mg capsule |
|---|---|
| Compound of the invention | 30.0 mg |
| Silicone | 2.9 mg |
| Starch Flowable | 267.1 mg |

EXAMPLE 5

Tablet Formulation

A tablet formulation is made by granulating the active with appropriate diluent, lubricant, disintegrant and binder and compressing

| Compound of the invention | 10.0 mg |
|---|---|
| Magnesium stearate | 0.9 mg |
| Microcrystalline cellulose | 75.0 mg |
| Povidone | 25.0 mg |
| Starch, directly compressible | 204.1 mg |

EXAMPLE 6

Aqueous Injection Formulation

An aqueous injection of active is prepared as a freeze-dried plug, for reconstitution in a suitable, sterile diluent before use (to a total volume of 10 ml).

Compound of the invention is contacted with Mannitol N Hydrochloric acid and/or N sodium hydroxide to adjust pH to 5–5.5.

| Compound of the invention | 20.0 mg |
|---|---|
| Manitol | 20.0 mg |
| N Hydrochloric acid and/or N sodium hydroxide to adjust pH to 5–5.5. | |

EXAMPLE 7

Controlled Release IM Formulation

A controlled release injection for intramuscular injection is formed from a sterile suspension of micronised active in an oleaginous vehicle.

| Compound of the invention | 50.0 mg |
|---|---|
| Aluminium stearate | 0.04 mg |
| Sesame oil | 2 ml |

EXAMPLE 8

Capsule Formulation

A formulation is prepared by blending the active with silicone starch and starch, and filling it into hard gelatine capsules.

| | Per 300 mg capsule |
|---|---|
| Compound of the invention | 2.5 mg |
| Starch flowable with 0.96% silicone 220 | 222.5 mg |
| Starch flowable | 75.0 mg |

EXAMPLE 9

2-methyl-4-(4-methyl-1-piperazinyl)-10H-thieno[2,3-b][1,5]benzodiazepine Granules The granules were produced by blending the mannitol and Hydroxymethyl propyl cellulose in a high shear mixer;

granulating with the aqueous suspension of 2-methyl-4-(4-methyl-1-piperazinyl)-10H-thieno[2,3-b][1,5]benzodiazepine and polysorbate 20; wet sized and subsequently dried in a fluid bed dryer. These are dry sized and reblended prior to packaging.

1a. 250 mg Sachets

| INGREDIENT | MG/SACHET |
|---|---|
| Active | |
| 2-methyl-4-(4-methyl-1-piperazinyl)-10H-thieno[2,3-b][1,5]benzodiazepine | 2.50 |
| Other Ingredients | |
| Mannitol | 234.97 |
| Hydroxypropyl methyl cellulose 3 cps | 12.50 |
| Polysorbate 20 | 0.028 |

Such granules are most preferably contacted with an acidic medium if a suspension or solution is desired.

What is claimed is:

1. A method for treating a tic disorder comprising administering to a mammal in need of such treatment, an effective amount 2-methyl-4-(4-methyl-1-piperazinyl)-10H-thieno[2,3-b][1,5]benzodiazepine, or a pharmaceutically acceptable salt thereof.

2. A method of claim 1 wherein the tic disorder is Tourette Disorder.

3. A method of claim 1 provided that the tic disorder is not Tourette Disorder.

4. A method of claim 1 wherein 2-methyl-4-(4-methyl-1-piperazinyl)-10H-thieno[2,3-b][1,5]benzodiazepine is substantially pure Form II 2-methyl-4-(4-methyl-1-piperazinyl)-10H-thieno[2,3-b][1,5]benzodiazepine having an X-ray powder diffraction pattern as follows, using a Sieman's D5000 diffractometer wherein d represents the interplaner spacing:

| d |
|---|
| 10.2689 |
| 8.577 |
| 7.4721 |

| d |
|---|
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007. |

5. A method of claim 4 wherein substantially pure Form II 2-methyl-4-(4-methyl-1-piperazinyl)-10H-thieno[2,3-b][1,5]benzodiazepine is free of solvates.

6. A method of claim 1 wherein the effective amount is from about 1 mg to about 20 mg per day.

7. A method of claim 1 wherein the tic disorder is a Transient Tic Disorder featuring one or more vocal tics.

8. A method of claim 1 wherein the tic disorder is drug-induced.

9. A pharmaceutical formulation for treating a tic disorder comprising an effective amount of 2-methyl-4-(4-methyl-1-piperazinyl)-10H-thieno[2,3-b][1,5]benzodiazepine as an active ingredient and one or more pharmaceutically acceptable carriers, wherein such formulation is packaged with a label or package insert indicating that such formulation can be useful for treating a tic disorder.

* * * * *